(12) United States Patent
Bardat et al.

(10) Patent No.: US 6,242,423 B1
(45) Date of Patent: Jun. 5, 2001

(54) FREEZE-DRIED PLACEBO PHARMACEUTICAL COMPOSITION DESIGNED TO IMITATE A MEDICINE, IN PARTICULAR BASED ON PROTEINS OR POLYPEPTIDES

(75) Inventors: Annie Bardat, Limours; Roland Schmitthauesler, Montigny le Bretonneux, both of (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

(21) Appl. No.: 09/508,831

(22) PCT Filed: Sep. 14, 1998

(86) PCT No.: PCT/FR98/01956

§ 371 Date: May 18, 2000

§ 102(e) Date: May 18, 2000

(87) PCT Pub. No.: WO99/13866

PCT Pub. Date: Mar. 25, 1999

(30) Foreign Application Priority Data

Sep. 18, 1997 (FR) .................................... 97 11626

(51) Int. Cl.$^7$ ............................ A01N 43/04; A01N 37/118
(52) U.S. Cl. ..................................... 514/23; 514/2; 514/53
(58) Field of Search ..................................... 514/23, 2, 53

(56) References Cited

FOREIGN PATENT DOCUMENTS

| 0 084 705 A2 | 8/1983 | (EP) . |
| 0 211 257 A2 | 2/1987 | (EP) . |
| 0 682 944 A1 | 11/1995 | (EP) . |
| 2 751 177 | 1/1998 | (FR) . |
| 51-51511 | 5/1976 | (JP) . |
| 9913866 A1 * | 3/1999 | (WO) . |

* cited by examiner

Primary Examiner—Louise N. Leary
(74) Attorney, Agent, or Firm—Foley & Lardner

(57) ABSTRACT

The invention discloses a lyophilized pharmaceutical composition designed to imitate a medicinal product containing proteins or peptides, free of medicinal product, and is capable of being used as a placebo, characterized in that the composition comprises an excipient for the medicinal product, one or more alcohol-sugars on crystalline form and/or one or more amino acids in crystalline form. The composition has osmolarity ranging between 250 and 650 milliosmoles after being restored in the form of solution. The pharmaceutical composition can be used for injection or for percutaneous or ocular application.

18 Claims, No Drawings

FREEZE-DRIED PLACEBO PHARMACEUTICAL COMPOSITION DESIGNED TO IMITATE A MEDICINE, IN PARTICULAR BASED ON PROTEINS OR POLYPEPTIDES

The invention relates to the pharmaceutical and medical field and is aimed at providing a fake version of a medicinal product in its usual pharmaceutical form, but not containing the active principle.

The invention applies most particularly to lyophilized pharmaceutical forms simulating medicinal products containing peptides or proteins obtained by extraction, from animal or human biological fluids, by genetic recombination, by synthesis or modified by directed chemical reactions or by genomic remodeling or by gene transfer.

These decoys can then be used for controlled double-blind clinical studies.

The placing of medicinal products on the market is conditioned by the results obtained by these products in controlled clinical studies, in which the experimenter proposes to measure the therapeutic effects of the active principles under study, relative to a control substance containing no active principle, known as a placebo. This artifice avoids the influence of uncontrollable factors associated with the subjectivity of the observations or the patient's condition. In these studies, a placebo should be offered whose appearance, consistency and observable properties are as close as possible to those of the real medicinal product. The manufacture of such placebos poses great difficulties when the substance to be studied is in the pharmaceutical form of a lyophilizate and when it contains active principles of protein or polypeptide nature.

Specifically, proteins or polypeptides have an amphiphilic nature and modify the surface tension of water, the usual solvent, thus leading to the formation of a layer of foam during the reconstitution of the medicinal product. Furthermore, the macromolecular structure of proteins or peptides gives the lyophilizate a behavior which is visualized in the form of a "cake" of dry, more or less thick substance, enclosed in the bottle. The placebo should contain no active principle; only the usual excipients of the medicinal product under study are permitted, accompanied, where appropriate, by one or more other inert substances.

Hitherto, the difficulties were solved by adding an inert macromolecule such as human albumin or injectable gelatin. The potential risks outlined recently, during the outbreak of neurodegenerative diseases in cattle and due to transmissible agents whose nature is still unknown, have led to these inert macromolecular substances no longer being tolerated in the manufacture of placebo, so that the receiver of the placebo does not incur an unevaluable risk.

There is therefore, in the current state of the art, no means for formulating a fake version of a medicinal product free of active principle of protein or polypeptide nature, which indiscernibly resembles the product containing the active principle.

To overcome this difficulty, it has been found that the consistency of the "cake" of lyophilizate of real product can be limited by lyophilizing a solution of the usual excipient(s) for the product (sugars, mineral salts, amino acids in amorphous form in the solid state) in the presence of an amino acid or a saccharide which is readily crystallizable, added in amounts such that the placebo composition reconstituted after lyophilization remains compatible with the isotonicity required for parenteral, intramuscular or subcutaneous injection or other application (percutaneous or ocular application).

The invention thus relates to a lyophilized pharmaceutical composition intended to imitate a medicinal product, based in particular on proteins or peptides, which is free of medicinal product, and which can serve as a placebo, characterized in that it comprises the usual excipient for said medicinal product, one or more alcohol-sugars in crystalline form and/or one [lacuna] more amino acids in crystalline form.

Generally, the usual excipient for the protein or polypeptide principle is a sugar chosen in particular from the group consisting of oligosaccharides, disaccharides and monosaccharides. Among the preferred monosaccharides are glucose or fructose, alone or as a mixture. Among the preferred disaccharides are sucrose, maltose or lactose, alone or as a mixture.

The usual excipient can also be an alkali metal or alkaline-earth metal salt or mixture of such salts (calcium or sodium citrate, phosphate, glutamate or acetate), one or more amino acids in amorphous form in the solid state, the addition of a suitable amount of crystallizable amino acids making the mixture crystalline in the lyophilized product according to the invention. In the case of placebo medicinal products simulating medicinal products containing peptides or polypeptides, the excipient should comprise no peptide or polypeptide.

The behavior of the dried product can be improved with excipients of high molecular mass: dextran, hydroxyethyl starch, polyethylene glycol, cyclodextrin, which are readily lyophilizable, but which require an addition of salts in order to maintain the osmolarity within acceptable values for parenteral use (particularly when it is a matter of injecting a large volume, from about 50 to 100 ml).

Preferably, the composition has an osmolarity of between 250 and 650 milliosmoles after reconstitution in solution form.

One preparation process consists in mixing together the various ingredients in solution and then in lyophilizing the solution obtained. During the preparation of the solution, the sugars or amino acids are "crystallizable", and this term will be used hereinbelow in this context. The term "crystalline" or "in crystalline form" is reserved for the finished lyophilized product.

Among the preferred crystallizable alcoholsugars are mannitol, sorbitol or a mixture thereof.

Among the preferred crystallizable amino acids are glycine, alanine, valine, leucine, lysine, glutamic acid, aspartic acid, arginine and histidine. These alcohol-sugars or amino acids crystallize readily during freezing of the starting solution, making it possible to obtain the lyophilized composition.

Furthermore, according to one preferred embodiment of the invention, the presence of nonionic surfactant which is compatible with parenteral use, in small amounts, gives the reconstituted placebo a foaming behavior which is comparable to that of the real product.

Among the nonionic surfactants which are mentioned are polysorbate, octoxynol, polyoxyethylenic alcohols or polyoxyethylenic esters of fatty acids. Mention is made in particular of Tween® 80.

Finally, in order to simulate the colloidal aspect of the real protein solution, it has been found that the controlled addition of a pharmaceutically acceptable metabolizable oil, or of an emulsified hydrolipidic compound, in small amounts gives a Tyndall effect which is comparable to that of the real product.

The expression "Tyndall effect" means the scattering of white light in the solution of macromolecules due to the light/protein interaction, giving this type of solution the "colloidal" aspect, which is a reflection of its polydispersity. Among the pharmaceutically acceptable oils which are mentioned are olive oil, corn oil, sunflower oil, soybean oil, castor oil, squalene or α-tocopherol. These oils are compatible with the parenteral route.

A typical emulsion of injectable lipids for parenteral administration can also be used (Intralipide®).

Certain proteins at high concentration have a slightly yellow to brown color. The placebos obtained according to the invention can simulate this color by addition of pharmaceutically acceptable colorants or by adding specific mixtures obtained by the Maillard reaction between a reducing sugar and an amino acid. Depending on the sugar and the amino acid chosen, the shades range from pale yellow to dark brown.

The compositions below are given from the process of preparation in solution (which step will be followed by the lyophilization). The proportions of the dried composition can readily be deduced from the solutions.

According to one preferred embodiment, the composition is characterized in that it can be obtained from a starting solution comprising, as a percentage by weight:

0.1 to 50% (W/V) usual excipient
0.1 to 20% (W/V) crystallizable amino acid or sugar
10 to 200 ppm surfactant
metabolizable oil or emulsified hydrolipidic compound and pigment (quantity sufficient to have the appearance of the medicinal product)

Advantageously, the solution comprises, as a percentage by weight:

usual excipient, less than or equal to 5% (W/V)
1 to 5% (W/V) crystallizable amino acid or sugar
50 to 100 ppm surfactant
metabolizable oil or emulsified hydrolipidic compound and pigment (quantity sufficient to have the appearance of the medicinal product).

The lyophilized composition is particularly suitable for presentation in injectable form, after reconstitution, or for percutaneous or ocular application after reconstitution.

Another aspect of the invention is the possibility of formulating a saccharide/excipient/amino acid or alcohol-sugar mixture such that the placebo can be produced according to a short lyophilization cycle, which does not harm the final aspect of the dried product.

A process for preparing such a lyophilized composition consists in adding, in the desired proportions, the various ingredients, in solution, and then in subjecting the solution to a freezing-lyophilization cycle. The examples which follow will assist the detailed understanding of the invention, while at the same time not limiting its field of application to the sole description of the applications carried out.

EXAMPLE 1

A solution is prepared containing 50 g/l of sucrose and 30 g/l of mannitol. 35 mg/l of Tween® 80are added. After distributing per 10 ml over a height of 2 cm per flask, the solution is frozen and lyophilized for 48 hours.

The dried placebo resembles the therapeutic product, and is reconstituted by adding water for injectable preparation, with formation of a foam. The reconstituted placebo has an osmolarity of 340 milliosmoles.

EXAMPLE 2

A solution is prepared containing 10 g/l of sucrose and 25 g/l of glycine. 25 mg/l of Tween® 80 are added. After distributing per 10 ml over a height of 2 cm per flask, the solution is frozen and lyophilized for 48 hours.

The dried placebo resembles the therapeutic product, and is reconstituted by adding water for injectable preparation, with formation of a foam. The reconstituted placebo has an osmolarity of 354 milliosmoles.

EXAMPLE 3

A solution is prepared containing 50 g/l of sucrose and 50 g/l of mannitol. 60 mg/l of Tween® 80and 0.065 ml/l of 10% Intralipid® are added. After distributing per 180 ml over a height of 4.5 cm, the solution is frozen and lyophilized for 90 hours.

The dried placebo resembles the therapeutic product, and is reconstituted by adding water for injectable preparation, with formation of a foam. The solution has a colloidal aspect. The reconstituted placebo has an osmolarity of 465 milliosmoles.

EXAMPLE 4

A solution is prepared containing 10 mM of trisodium citrate and 50 g/l of mannitol. 35 mg/l of Tween® 80 are added. After distributing per 10 ml over a height of 1 cm, the solution is frozen and lyophilized for 35 hours.

The dried placebo resembles the therapeutic product, and is reconstituted by adding water for injectable preparation, with formation of a foam. The reconstituted placebo has an osmolarity of 334 milliosmoles.

EXAMPLE 5

A solution is prepared containing 44 g/l of sucrose, 35 g/l of mannitol, 1.75 g/l of sodium chloride and 0.05 g/l of Tween® 80. After distributing per 180 ml over a height of 4.5 cm, the solution is frozen and lyophilized for 100 hours.

The dried placebo resembles the therapeutic product, and is reconstituted by adding water for injectable preparation, with formation of a foam. The reconstituted placebo has an osmolarity of 407 milliosmoles.

COMPARATIVE EXAMPLE 10 ml of a 10% sucrose solution are lyophilized over a thickness of 2 cm under the following conditions:

Freezing temperature: −50° C.
Primary desiccation temperature: −38° C. in the product
Secondary desiccation temperature: +40° C.
Duration of the cycle: 180 hours At the end of such a cycle, the only compound is found in the form of a "cake". The reconstituted placebo has an osmolarity of 314 milliosmoles. However, it will be noted that the duration of the cycle is 180 hours, which is a prohibitive duration for any industrial application.

What is claimed is:

1. A lyophilized pharmaceutical composition designed to imitate a medicinal product containing proteins or peptides, free of medicinal product, and capable of being used as a placebo, characterized in that the composition comprises an excipient for said medicinal product, one or more alcohol-sugars in crystalline form and/or one more amino acids in crystalline form.

2. The pharmaceutical composition according to claim 1, characterized in that the excipient is selected from the group consisting of oligosaccharides, disaccharides and monosaccharides.

3. The pharmaceutical composition according to claim 2, characterized in that the monosaccharide is glucose or fructose or a mixture of these monosaccharides.

4. The pharmaceutical composition according to claim 2, characterized in that the disaccharide is sucrose, maltose or lactose or a mixture of these disaccharides.

5. The pharmaceutical composition according to claim 1, characterized in that the excipient is selected from suitable salts.

6. The pharmaceutical composition according to claim 5, characterized in that the salts are chosen from citrates, phosphates, glutamates and acetates.

7. The pharmaceutical composition according to claim 1, characterized in that said excipient is chosen from amino acids which are in amorphous form in the solid state.

8. Pharmaceutical composition according to one of the preceding claims 1 to 7, characterized in that the alcohol-sugar is mannitol or sorbitol or a mixture of these alcohol-sugars.

9. The pharmaceutical composition according to one of claims 1 to 7, characterized in that the amino acid is glycine, alanine, valine, leucine, lysine, glutamic acid, aspartic acid, arginine, histidine or a mixture of two or more of the amino acids mentioned.

10. The pharmaceutical composition according to claim 1, characterized in that pharmaceutical composition contains a nonionic surfactant.

11. The pharmaceutical composition according to claim 10, characterized in that the nonionic surfactant is polysorbate, octoxynol, polyoxyethylenic alcohols or polyoxyethylenic esters of fatty acids.

12. Pharmaceutical composition according to claim 1, characterized in that said pharmaceutical composition has a colloidal aspect and comprises a pharmaceutically acceptable metabolizable oil such as olive oil, corn oil, sunflower oil, soybean oil, castor oil, squalene or α-tocopherol.

13. The pharmaceutical composition according to claim 1, characterized in that said pharmaceutical composition has a colloidal aspect and comprises an emulsified lipid composition.

14. Pharmaceutical composition according to claim 1, characterized in that the color is adjusted by adding an authorized colorant or a Maillard reaction product ranging from yellow to dark brown.

15. Pharmaceutical composition according to claim 1, characterized in that said composition has an osmolarity of between 250 and 650 milliosmoles after reconstitution in solution form.

16. Pharmaceutical composition according to claim 1, characterized in that said pharmaceutical composition can be obtained from a starting solution comprising, as a percentage by weight:

0.1 to 50% (W/V) usual excipient 0.1 to 20% (W/V) crystallizable amino acid or sugar 10 to 200 ppm surfactant metabolizable oil or emulsified hydrolipidic compound and pigment in a quantity sufficient to have the appearance of the medicinal product.

17. Pharmaceutical composition according to claim 1, characterized in that said pharmaceutical composition is in injectable form.

18. The pharmaceutical composition according to claim 1, characterized in that said pharmaceutical composition is in the form of a percutaneous or ocular application.

* * * * *